(12) United States Patent
van Beek

(10) Patent No.: US 10,772,754 B2
(45) Date of Patent: Sep. 15, 2020

(54) ORTHOTIC DEVICE FOR INHIBITING A SUBJECT'S CHEST EXPANSION

(71) Applicant: Inter Medical Services Ltd, Guernsey, (Channel Islands) (GB)

(72) Inventor: Rainier van Beek, Prajuabkirikhan (TH)

(73) Assignee: Rainier van Beek, Prachuap Khiri Khan (TH)

(*) Notice: Subject to any disclaimer, the term of this patent is extended or adjusted under 35 U.S.C. 154(b) by 310 days.

(21) Appl. No.: 14/676,296

(22) Filed: Apr. 1, 2015

(65) Prior Publication Data

US 2016/0120685 A1   May 5, 2016

(30) Foreign Application Priority Data

Nov. 5, 2014  (TH) .................................. 1401006638

(51) Int. Cl.
*A61F 5/00*    (2006.01)
*A61F 5/02*    (2006.01)
(Continued)

(52) U.S. Cl.
CPC .................. *A61F 5/02* (2013.01); *A61F 5/03* (2013.01); *A61F 5/058* (2013.01)

(58) Field of Classification Search
CPC .... A61F 5/02; A61F 5/03; A61F 5/026; A61F 5/028; A61F 5/058; A61F 5/37; A61F 5/3746; A61F 5/022; A61F 5/024; A61F 5/0553; A41D 13/04; A41D 13/0518; A41D 13/0525; A41D 13/0531; A61G 7/1015; A63B 21/15; A63B 21/151; A44B 11/02;
(Continued)

(56) References Cited

U.S. PATENT DOCUMENTS 2,440,012 A  *  4/1948  Haver ................... G09F 3/0352
                                                    24/30.5 R
4,641,642 A  *  2/1987  Williams, Jr. ............ A61F 5/03
                                                      128/875
(Continued)

FOREIGN PATENT DOCUMENTS

DE             162640         3/1949
EP            0260351         3/1988
WO         2010077144         7/2010

*Primary Examiner* — Keri J Nelson
*Assistant Examiner* — Adam Baker
(74) *Attorney, Agent, or Firm* — Armis IP Law, LLC

(57) ABSTRACT

In some embodiments, a method and/or system may include an orthotic device configured to limit expansion of a subject's chest. The orthotic device may include an elongated band, a pulley assembly, and a locking mechanism. The elongated band wraps, during use, around a chest of a subject comprising a first end couplable to a first base and a second end couplable to a second base. An elongated member, of the pulley assembly, may couple a first routing member to a second routing member such that by applying, during use, a pulling force to the elongated member a distance between the first and the second routing members decreases. The routing members may be removably coupled to the respective bases. The pulley assembly may include a locking mechanism which inhibits movement of the elongated member relative to at least one of the routing members such that the distance is inhibited from increasing.

25 Claims, 10 Drawing Sheets

(51) Int. Cl.
*A61F 5/058* (2006.01)
*A61F 5/03* (2006.01)

(58) Field of Classification Search
CPC ............... A44B 19/303; Y10T 24/3911; Y10T 24/3918; Y10T 24/3936; Y10T 24/3942; Y10T 24/4019; Y10T 24/4044; Y10T 24/3913; Y10T 24/3929; Y10T 24/3993; A61B 17/12009; A61H 1/0296; A61H 1/0292; A61H 1/02; A61H 1/0222; A61H 1/0229; A61H 1/0218
USPC ........... 602/19, 20, 21, 5, 6, 62, 63; 482/13; 128/869, 874–875, 96.1, 100.1
See application file for complete search history.

(56) References Cited

U.S. PATENT DOCUMENTS

| | | | |
|---|---|---|---|
| 6,213,968 B1* | 4/2001 | Heinz | A61F 5/028 602/19 |
| 6,322,529 B1* | 11/2001 | Chung | A61F 5/028 2/319 |
| 6,517,502 B2 | 2/2003 | Heyman et al. | |
| 2001/0034498 A1* | 10/2001 | Heyman | A61F 5/03 602/19 |
| 2002/0148461 A1* | 10/2002 | Heinz | A61F 5/03 128/96.1 |
| 2005/0251074 A1* | 11/2005 | Latham | A61F 5/028 602/19 |
| 2010/0262053 A1* | 10/2010 | Crago | A61F 5/026 602/6 |
| 2014/0135672 A1* | 5/2014 | Joseph | A61F 5/028 602/19 |

\* cited by examiner

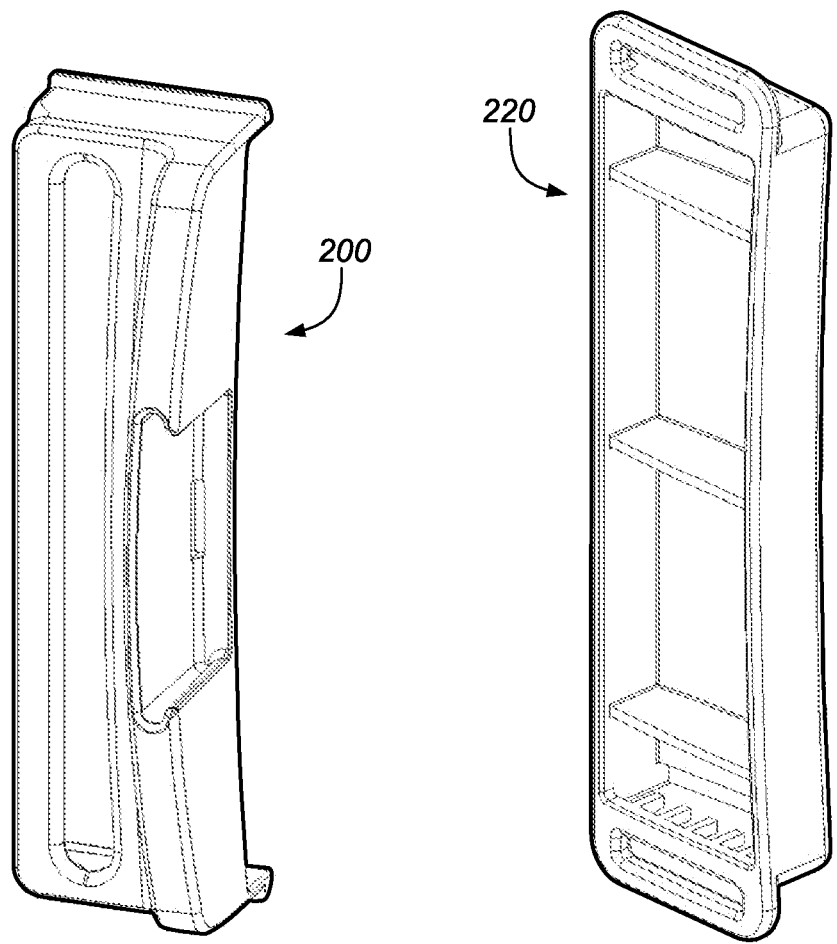
FIG. 6A
FIG. 6B
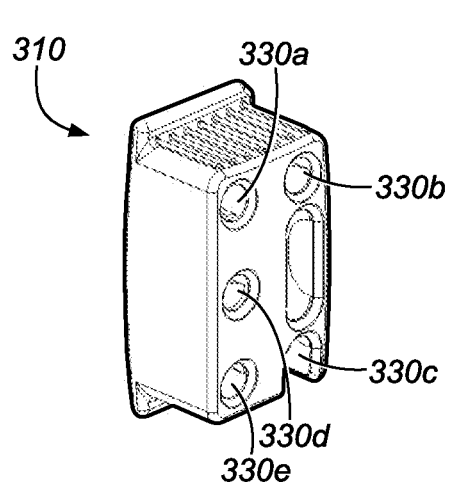
FIG. 7A
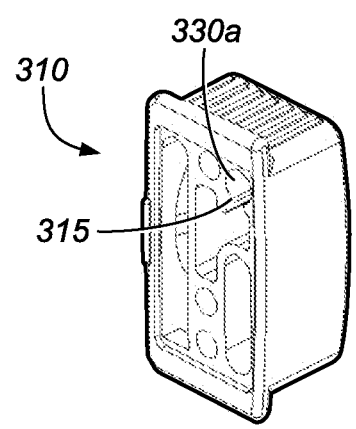
FIG. 7B

ORTHOTIC DEVICE FOR INHIBITING A SUBJECT'S CHEST EXPANSION

PRIORITY CLAIM

This application claims priority to Thailand Patent Application No. 140100638 entitled "BAND ASSEMBLY FOR STERNUM REPAIR" filed on Nov. 5, 2014, which is incorporated by reference herein.

BACKGROUND OF THE INVENTION

1. Field of the Invention

The present disclosure generally relates to a device for the repair of split portions of bone and tissue. More particularly, the disclosure generally relates to a method and system for securing a band around split portions of a sternum to maintain the split portions in an adjacent contact relationship during the healing process.

2. Description of the Relevant Art

Many cardiac operations may be performed by a median sternotomy. A median sternotomy is a vertical incision of the breastbone/sternum after which the sternum is cracked open. This provides access to the heart, arteries, lungs, thorax, etc. After surgery, the two halves of the breastbone/sternum are sewn together with steel wires, leaving a large wound to heal. Previous band assemblies do help to inhibit expansion of a subject's chest. Previous band assemblies incorporate mechanisms that do not provide the flexibility of retaining a band in a closed looped locking configuration around the sternum portions that could be used in different manners according to the need of each patient during the healing process. Previous band assemblies do not incorporate simplified contracting and/or locking mechanisms for band assembly orthotic devices.

Accordingly, there exists a need for an improved orthotic device for, for example, sternum repair which is relatively easy to use, yet still effectively secures the sternum portions together during healing.

SUMMARY

In some embodiments, a method and/or system may include an orthotic device configured to limit expansion of a subject's chest. The orthotic device may include an elongated band, a pulley assembly, and a locking mechanism. The elongated band wraps, during use, around a chest of a subject comprising a first end couplable to a first base and a second end couplable to a second base. An elongated member, of the pulley assembly, may couple a first routing member to a second routing member such that by applying, during use, a pulling force to the elongated member a distance between the first and the second routing members decreases. The first routing member may be removably coupled to the first base. The second routing member may be removably coupled to the second base. The pulley assembly may include a locking mechanism which when activated inhibits, during use, movement of the elongated member relative to at least one of the routing members such that the distance is inhibited from increasing. When the locking mechanism is activated the elongated member is moved from a first opening with a first diameter to a second opening with a second smaller diameter.

BRIEF DESCRIPTION OF THE DRAWINGS

Advantages of the present invention may become apparent to those skilled in the art with the benefit of the following detailed description of the preferred embodiments and upon reference to the accompanying drawings.

FIGS. 6A-B depict a perspective view of a representation of an embodiment of a grip and a grip base respectively of a orthotic device.

FIGS. 7A-B depict perspective views of a representation of an embodiment of a routing member.

Figure 1A:
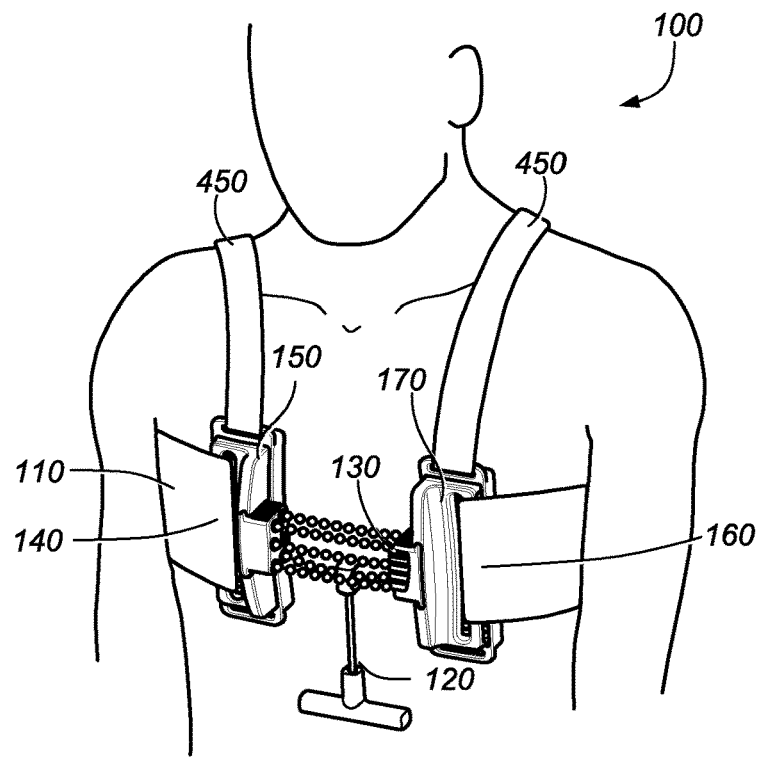
FIGS. 1A-B depict a perspective view of a representation of two embodiments of a orthotic device in an inactivated state being worn by a subject.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "third die electrically connected to the module substrate" does not preclude scenarios in which a "fourth die electrically connected to the module substrate" is connected prior to the third die, unless otherwise specified. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112 paragraph (f), interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

Accordingly, there exists a need for an improved orthotic device for, for example, sternum repair which is relatively easy to use, yet still effectively secures the sternum portions together during healing. In some embodiments, a method and/or system may include an orthotic device configured to limit expansion of a subject's chest. An orthotic device may be used to limit expansion of a subject's chest for which such limitation is beneficial to a subject (e.g., broken ribs, painful/debilitating coughing, abdominal bracing, back bracing, thoracotomy).

Figure 1B:
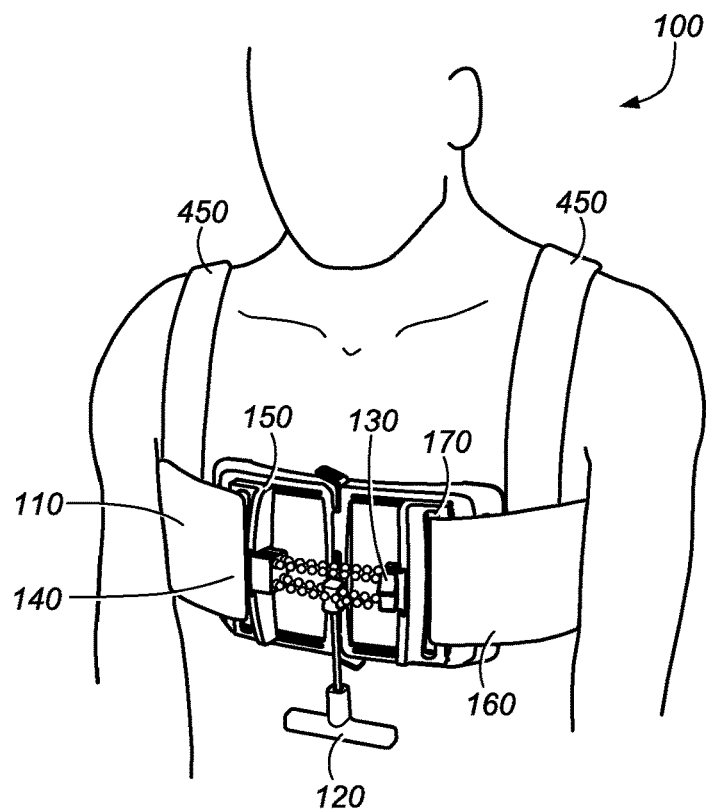
Figure 2A:
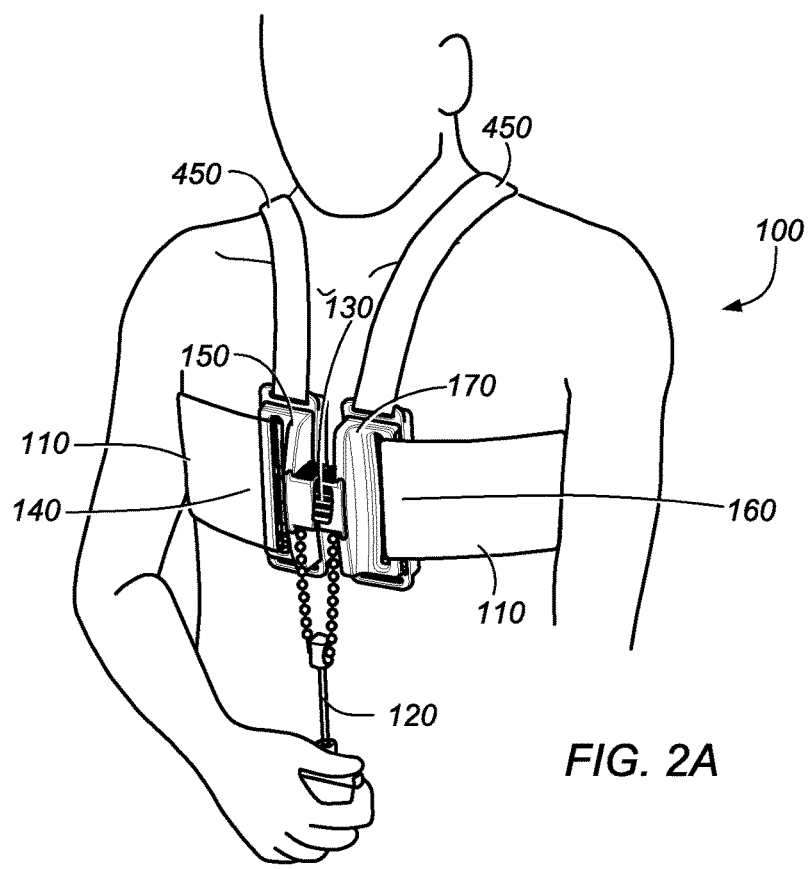
FIGS. 2A-B depict a perspective view of a representation of two embodiments of a orthotic device in an activated state when a pulling force is applied to the cord.
Figure 2B:
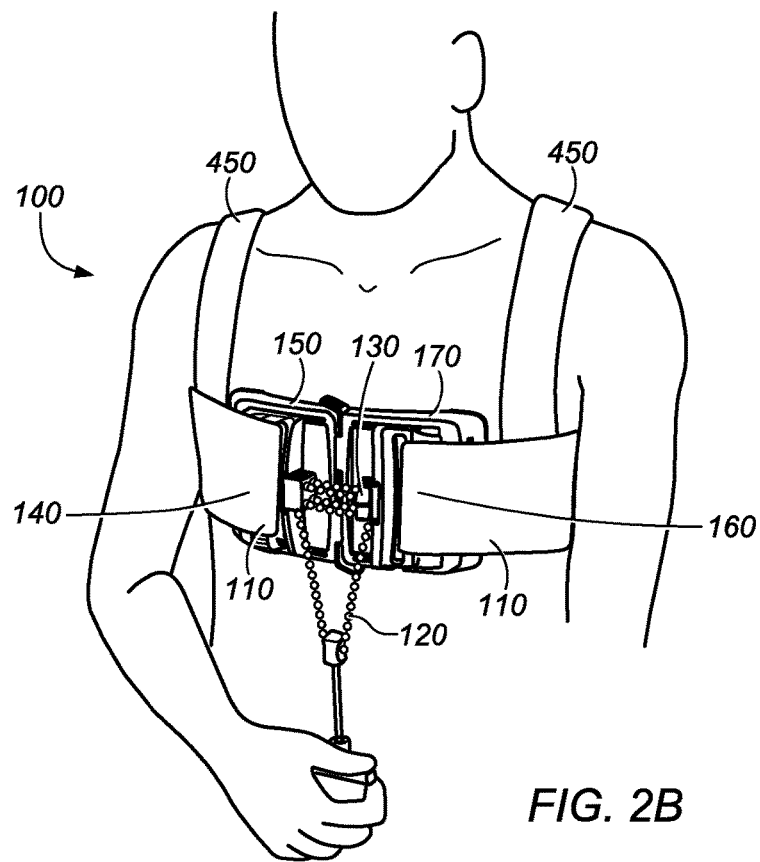

In some embodiments, a method and/or system may include an orthotic device configured to limit expansion of a subject's chest. The orthotic device may include an elongated band 110, a pulley assembly 120, and a locking mechanism 130. The elongated band may wrap, during use, around a chest of a subject comprising a first end 140 couplable to a first base 150 and a second end 160 couplable to a second base 170. Chest as used herein may refer to the thorax. Chest as used herein may refer to the thorax and the abdomen or at least the thorax and the upper abdomen. FIGS. 1A-B depict a perspective view of a representation of two embodiments of a orthotic device 100 in an inactivated state being worn by a subject. In an inactivated state the orthotic device 100 may not inhibit or limit expansion of a subject's chest. FIGS. 2A-B depict a perspective view of a representation of two embodiments of a orthotic device 100 in an activated state when a pulling force is applied to the cord. Upon activation the orthotic device may contract such that a diameter of the orthotic device, during use, may reduce. In an activated state the orthotic device may inhibit or limit expansion of a subject's chest.

In some embodiments, the elongated band may be formed from a flexible material (e.g., fabric formed from natural fibers, synthetic fibers, or a combination of both). In some embodiments, the elongated band may be formed from a substantially inelastic material.

Figure 3A:
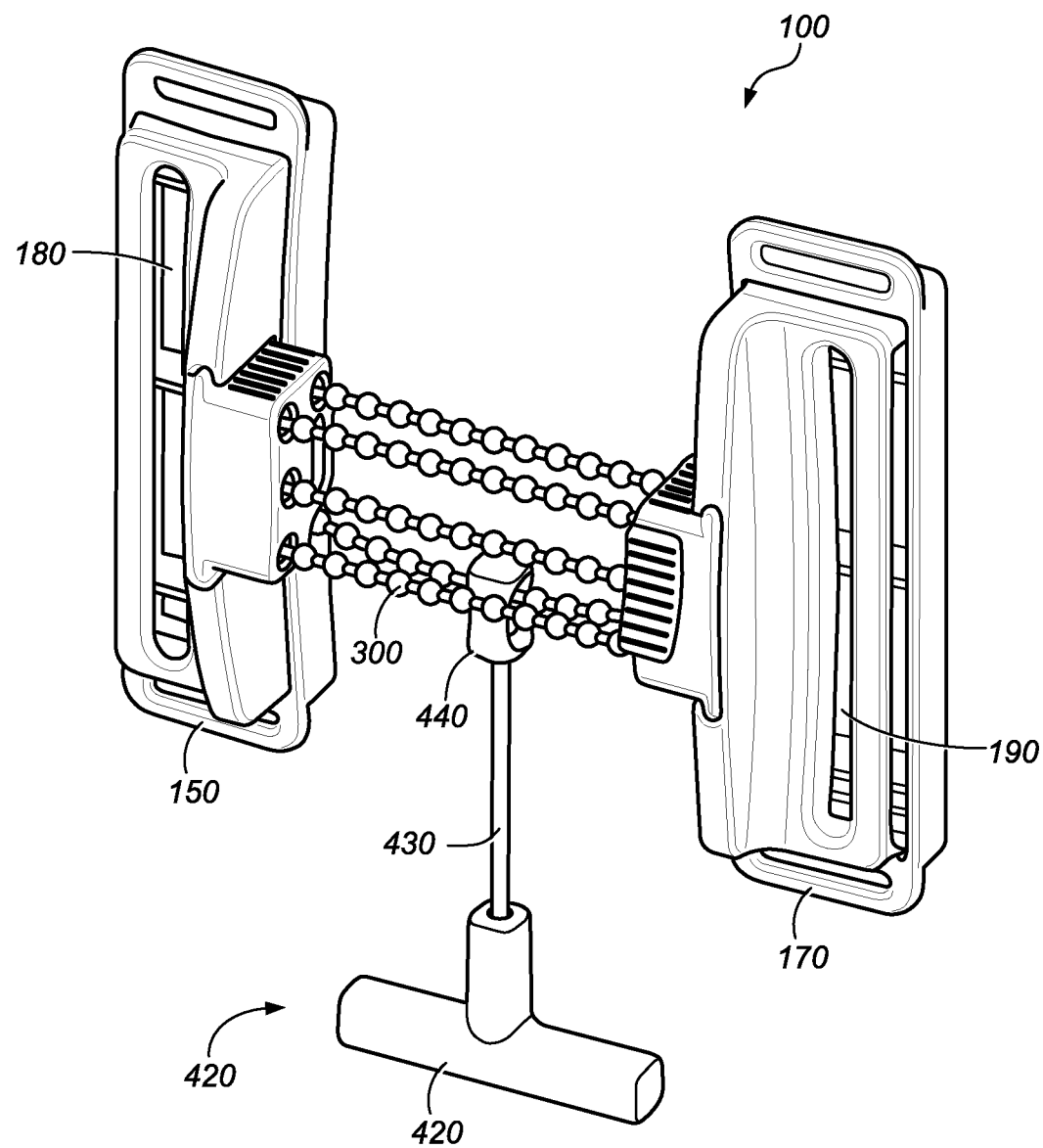
FIGS. 3A-B depict a perspective view of a representation of two embodiments of a orthotic device with the integration of the pulley assembly.
Figure 3B:
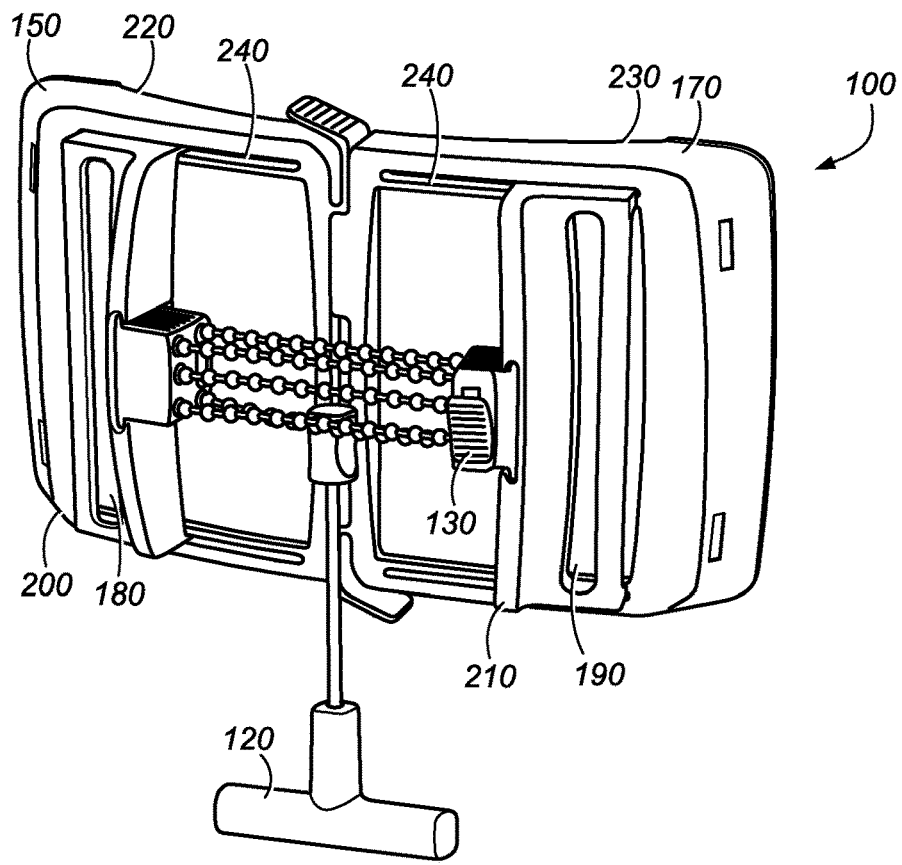
Figure 3C:
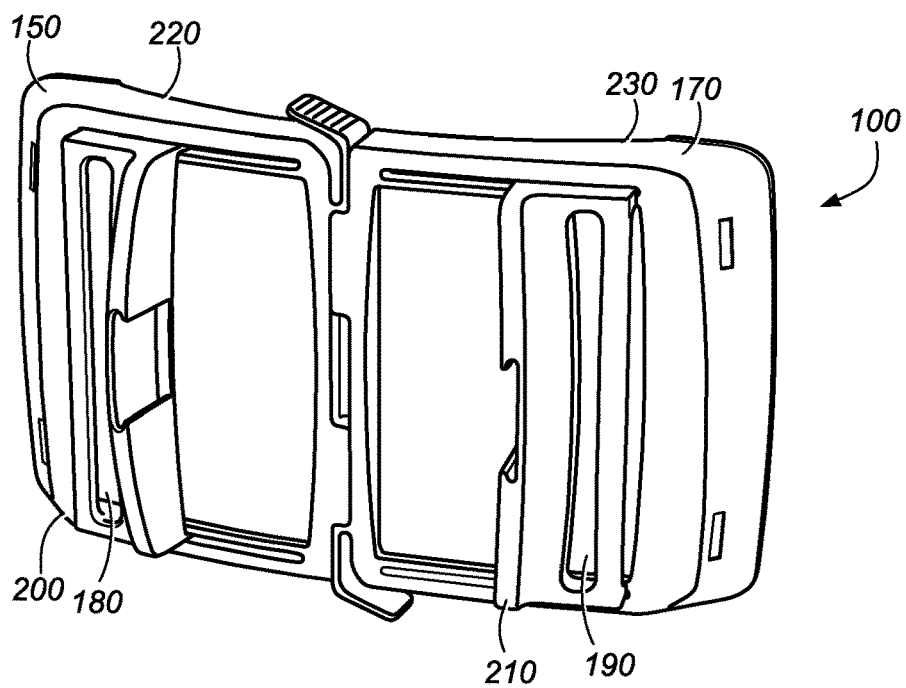
FIG. 3C depicts a perspective view of a representation of the embodiment of an orthotic device depicted in FIG. 3B without the pulley assembly.

In some embodiment's, the first base 150 may be configured to be removably coupled to the first end 140 of the elongated band 110 and the second base may be configured to be removably coupled to the second end of the elongated band (e.g., as depicted in FIGS. 1A-2B). An end of the elongated band may be coupled to a base such that a length of the elongated band may be adjusted. In some embodiments, the elongated band may be coupled to a base using a hook and loop system (e.g., the elongated band directly attached to the base and/or the elongated band looped through an opening in the base and attached to itself using hook and loop). In some embodiments, an end of the elongated band may be positioned through an opening 180-190 running through the respective bases 150, 170 (e.g., as depicted in FIGS. 3A-C). Looping the elongated band through the opening may allow an end of the elongated band to be coupled to another portion of the elongated band allowing adjustment of the length of the elongated band. One or both ends of the elongated band may be removably and/or adjustably coupled to the bases.

Figure 4A:
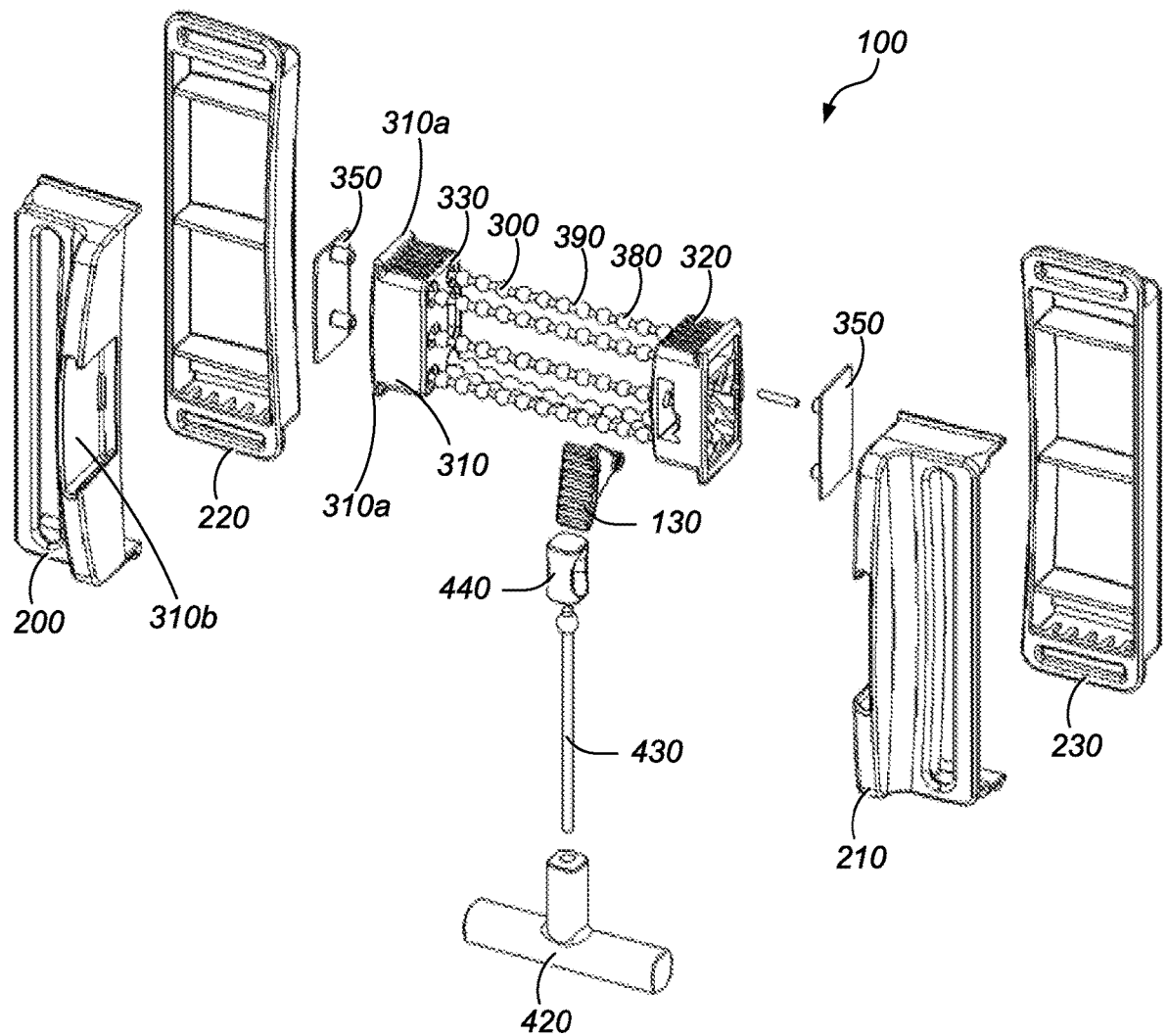
FIGS. 4A-B depict an exploded perspective view of a representation of two embodiments of a orthotic device with the integration of the pulley assembly.

In some embodiments, a base 150, 170 may include a grip 200, 210 and a grip base 220, 230 (e.g., as depicted in FIGS. 4A-B and 6A-B). In some embodiments, the grip may be coupled to the grip base such that the grip does not move relative to the grip base during use (e.g., as depicted in FIG. 4A).

In some embodiments, the grip 200, 210 may be coupled to the grip base 220, 230 such that the grip moves relative to the grip base during use (e.g., as depicted in FIGS. 3B-C). Portions of the grip may be positioned in openings 240 or tracks (e.g., using an interference fit) such that the grip may move relative (e.g., slide along the tracks) to the grip base. Adjustable grips may allow a diameter of the elongated band during use to contract thereby inhibiting chest expansion of the subject (e.g., a subject may engage the grips and move the grips towards each other relative to the grip bases). In some embodiments, the grips may be locked (e.g., using a ratcheting mechanism) into position without the use of the pulley assembly or locking mechanism disclosed herein.

Figure 4B:
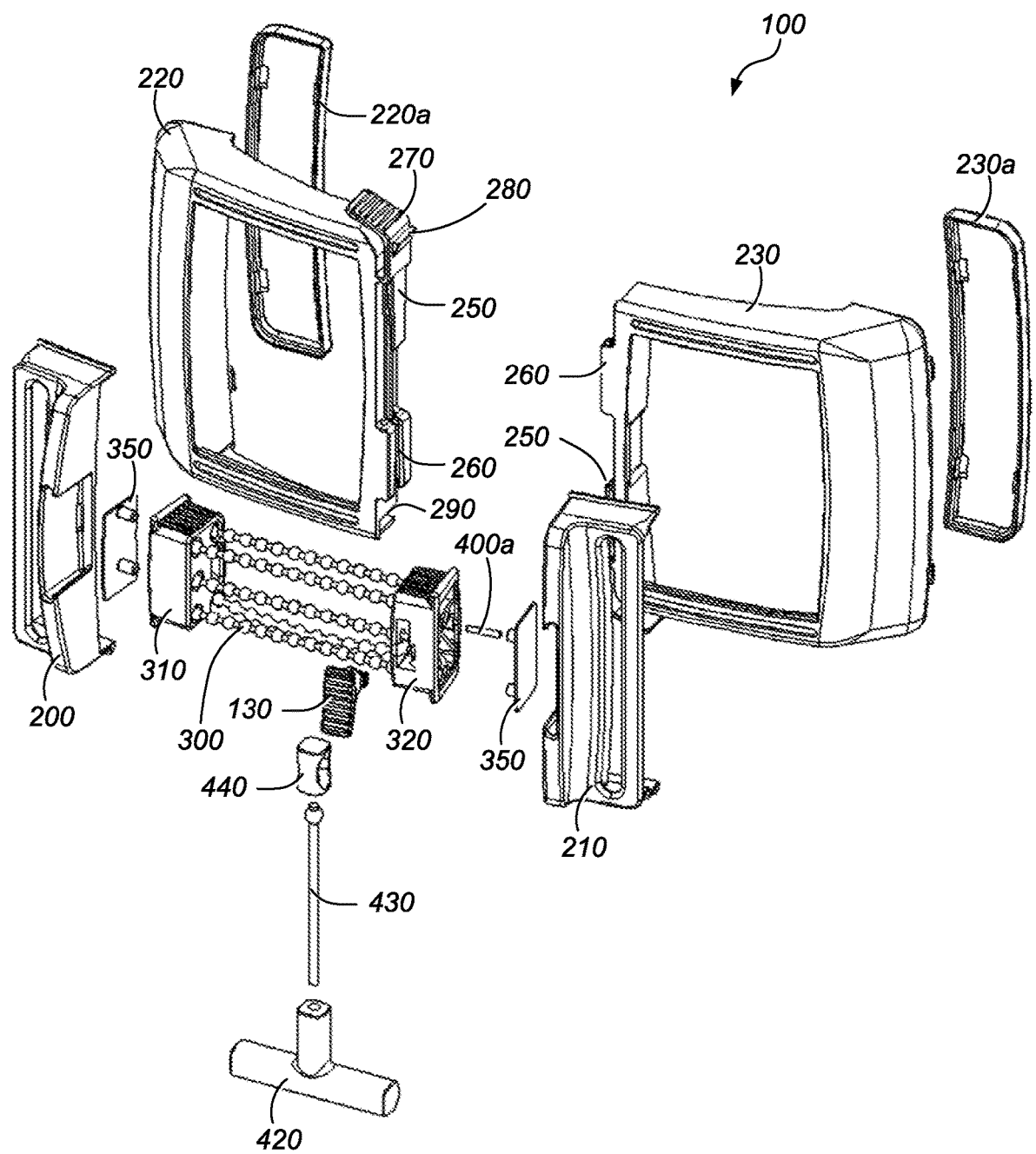

In some embodiments, the grip bases 220, 230 may be couplable to one another during use (e.g., as depicted in FIGS. 3B-C). The grip bases may couple to one another using one or more interference fits. For example, shaped portions 250 of the grip bases may fit into complementary shaped channels 260 on the opposing grip base (e.g., as depicted in FIG. 4B). Locks may be used to inhibit separation of the grip bases. Locks may include flexible tabs 270 with extensions 280 which fit into complementary shaped openings 290 on the opposing grip base (e.g., as depicted in FIG. 4B). In some embodiments, the grip base may include a support 220a, 230a (e.g., as depicted in FIG. 4B). In some embodiments, the grip base may include a flexible pad. The flexible pad may inhibit discomfort caused by the orthotic device especially when activated inhibiting expansion of the subject's chest.

In some embodiments, the orthotic device 100 may include an assembly which functions to facilitate contraction of the diameter of the elongated band during use. The assembly may include a pulley assembly 120. The pulley assembly may include an elongated member 300 coupling a first routing member 310 to a second routing member 320 (e.g., as depicted in FIGS. 4A-B). The elongated member 300 may couple the first routing member 310 to the second routing member 320 by routing the elongated member through a plurality of first 330 and second 340 openings in the respective first 310 and second 320 routing members (e.g., as depicted in FIGS. 7A-B and 8A-B). The elongated member 300 may include a single continuous elongated member which threads in and out of openings in a routing member(s) such that the routing member(s) function as a pulley. A pulley system has mechanical advantages which facilitates activation/contraction of the elongated band of the orthotic device. Pulleys are assembled to form a block and tackle in order to provide mechanical advantage (i.e., multiply the applied force) to apply large forces. The pulley system may allow the extremely young, old, and/or physically disabled to apply a greater contraction force to the elongated band than they might normally be able to without assistance.

Figure 8A:
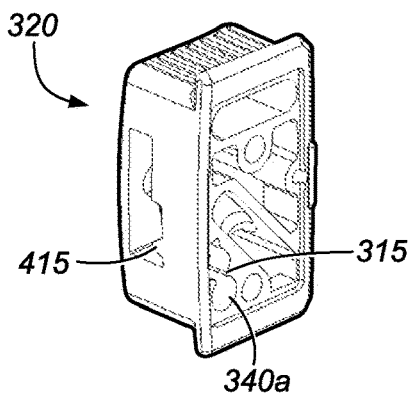
FIGS. 8A-B depict perspective views of a representation of an embodiment of a routing member.
Figure 8B:
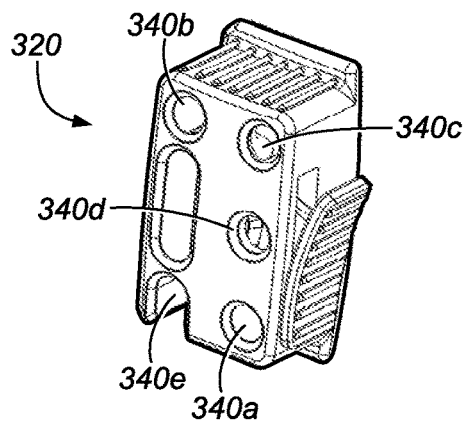
Figure 9:
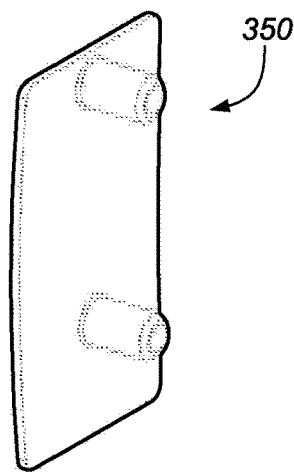
FIG. 9 depicts a perspective view of a representation of an embodiment of a rear cover of a routing member.

The elongated member, of the pulley assembly, may couple a first routing member to a second routing member such that by applying, during use, a pulling force to the elongated member a distance between the first and the second routing members decreases (e.g., as depicted in FIGS. 1A and 2A, 1B and 2B). Decreasing the distance between the routing members may move the elongated band from an expanded state to a contracted state such that when the elongated band is in the contracted state the first and the second end of the elongated band are drawn towards each other limiting expansion of a subject's chest. In some embodiments, a first end of the elongated member is directly attached to the first routing member 310 (e.g., via an opening 330a and locked into place using notches 315 as depicted in FIGS. 7A-B) and a second end of the elongated member is directly attached to the second routing member 320 (e.g., via an opening 340a and locked into place using notches 315 as depicted in FIGS. 8A-B). FIGS. 7A-B and 8A-B depict the routing members with a rear cover 350 removed (e.g., as depicted in FIG. 9). The elongated member may rout in and out of the first routing member 310 such that one or more portions function as a pulley (e.g., openings 330b-c function as a pulley and openings 330d-e function as a pulley as depicted in FIG. 7A). The elongated member may rout in and out of the first routing member 320 such that one or more portions function as a pulley (e.g., openings 340b-c function as a pulley and openings 340d-e function as a pulley as depicted in FIG. 8B).

In some embodiments, the first routing member may be removably coupled to the first base. The second routing member may be removably coupled to the second base. The first routing member may be couplable to the first base by positioning a portion of the routing member 310a within a complementary shaped opening 310b in the first base (e.g., as depicted in FIG. 4A).

The pulley assembly 120 may include a locking mechanism 130 which when activated inhibits, during use, movement of the elongated member relative to at least one of the routing members such that the distance is inhibited from increasing. In some embodiments, when the locking mechanism is activated the elongated member is moved from a first opening 360 with a first diameter to a second opening 370 with a second smaller diameter forming an interference fit with the elongated member (e.g., as depicted in FIG. 10).

In some embodiments, the elongated member may include a pattern of alternating first 380 and second 390 diameters (e.g., as depicted in FIG. 4A), wherein the second diameter is less than the first diameter. The locking mechanism may include an opening with a third diameter and a fourth diameter. The third diameter may be greater than the first diameter. The fourth diameter may be less than the first diameter and greater than the second diameter such that when a portion of the elongated member with the second diameter is positioned in the opening with the fourth diameter the elongated member is inhibited from further movement relative to the locking mechanism (and consequently inhibiting inactivation of the orthotic device from the active/contracted state to the inactive/expanded state). The larger first diameter portions of the elongated member may include substantially spherical beads coupled to and/or formed with the elongated members and a string and/or cord connecting the beads functions as the portions of the elongated member with the smaller second diameter portions. The elongated member may include a beaded chain. The elongated member may be formed from polymers, metal, natural fibers, synthetic fibers, etc.

Figure 5A:
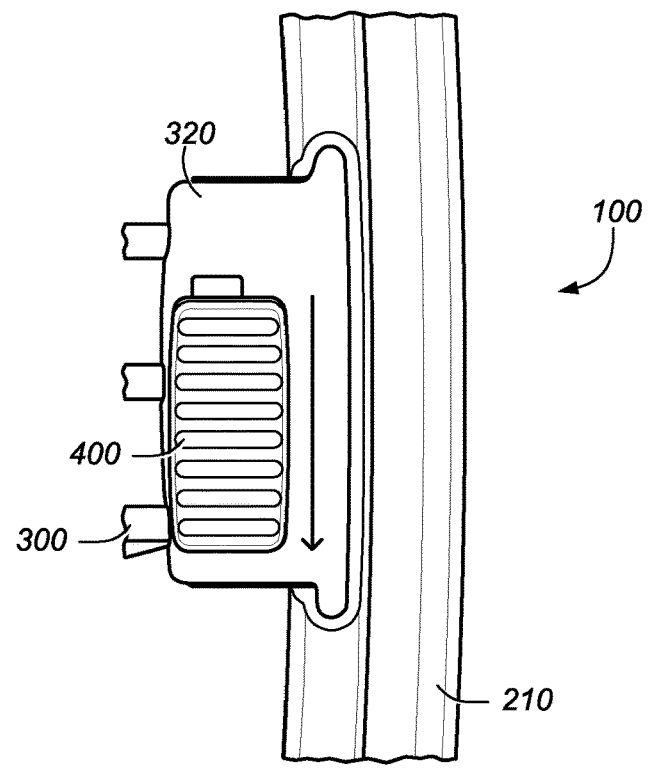
FIGS. 5A, C depict a perspective view of a representation of two embodiments of a locking mechanism in an unlocked state.
Figure 5B:
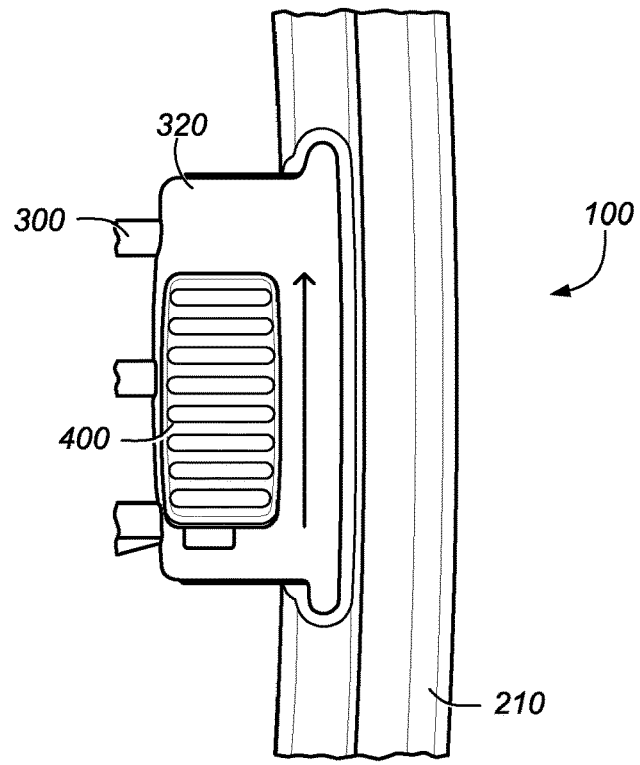
FIGS. 5B, 5D depict a perspective view of a representation of two embodiments of a locking mechanism in a locked state.
Figure 5C:
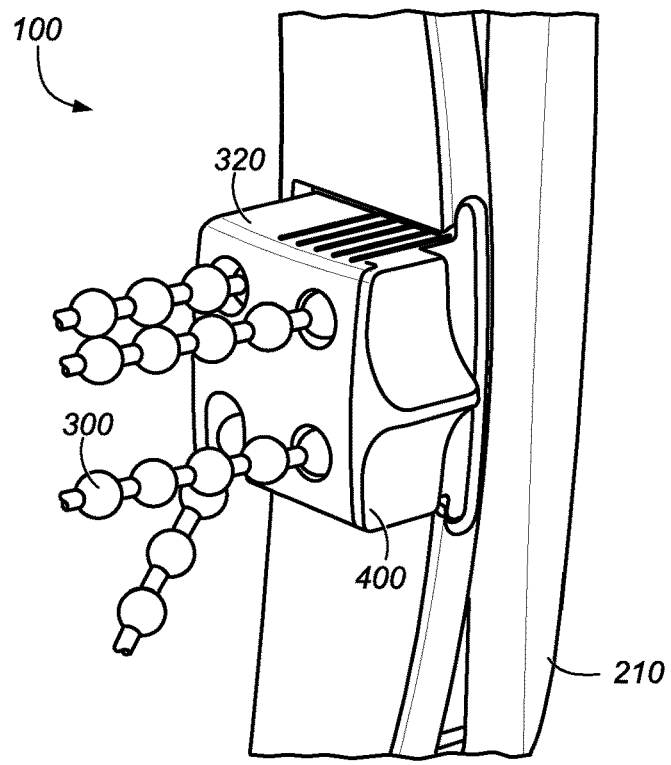
Figure 5D:
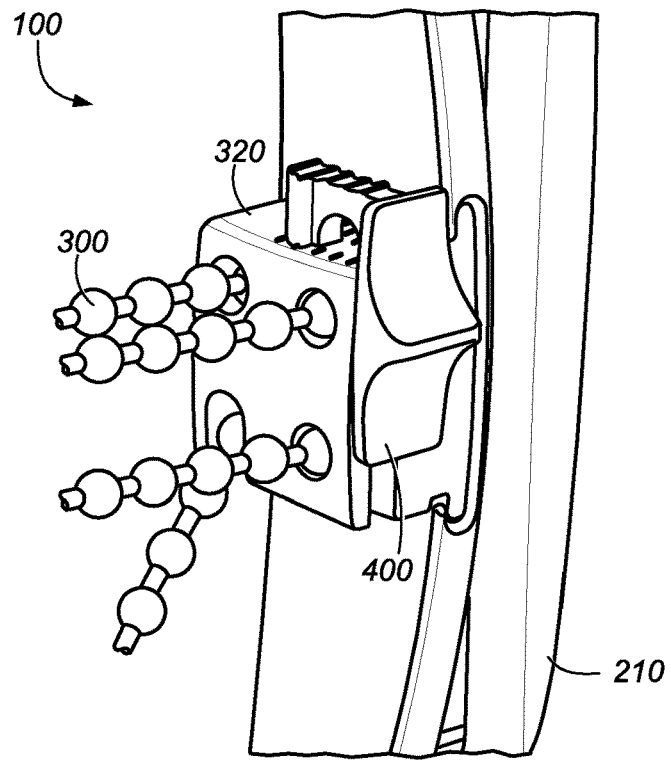
Figure 10:
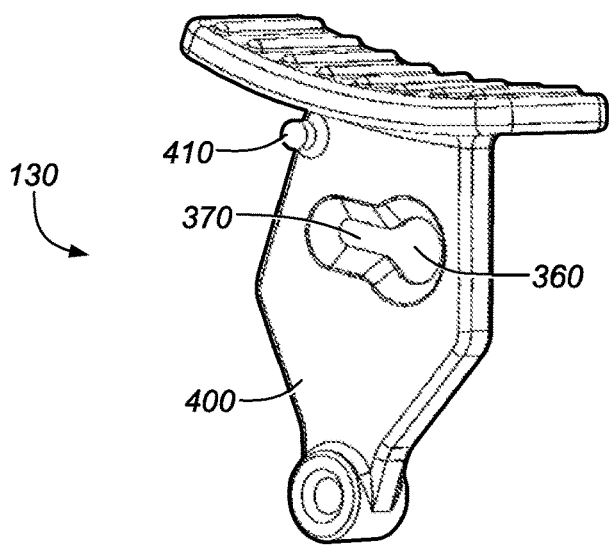
FIG. 10 depicts a perspective view of a representation of an embodiment of a locking member of a locking mechanism.

The locking mechanism may include a movable portion 400 wherein the variable diameter opening extends through the moveable portion (e.g., as depicted in FIG. 10). In some embodiments, the locking mechanism may include a securing mechanism which inhibits movement of the movable portion from at least a first position. In some embodiments, the locking mechanism may include a securing mechanism which inhibits movement of the movable portion 400 from at least a first position and a second position. In some embodiments, the first position may include a locked position (e.g., as depicted in FIGS. 5B and 5D) such that once the locking mechanism is activated the locking mechanism is inhibited from being inactivated/unlocked and the second position may include an unlocked position (e.g., as depicted in FIGS. 5A and 5C). The securing mechanism may include an interference fit (e.g., a first extension 410 (e.g., as depicted in FIG. 10) coupled to the movable portion 400 and a second extension 415 coupled to the routing member 320 (e.g., as depicted in FIG. 8A) to which the movable portion is movably coupled to). The movable portion may be rotationally (e.g., as depicted in FIGS. 5A-B (via a pin 400a as depicted in FIG. 4B)) or slidingly (e.g., as depicted in FIGS. 5C-D) coupled to the routing member.

Figure 11:
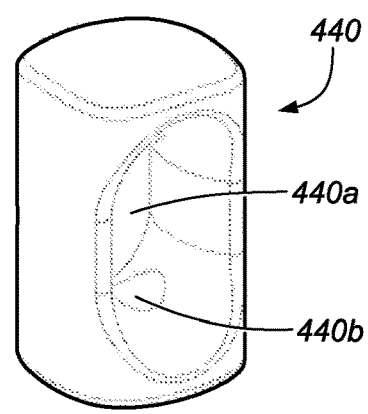
FIG. 11 depicts a perspective view of a representation of an embodiment of a coupler.
Figure 12:
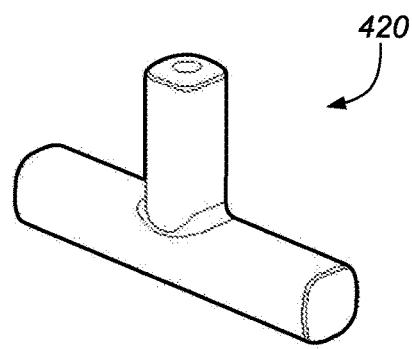
FIG. 12 depicts a perspective view of a representation of an embodiment of a cord grip.

In some embodiments, the orthotic device may include a gripping member 420 coupled to the elongated member (e.g., between the routing members as depicted in FIG. 3A). The gripping member (e.g., a handle, a T-handle, etc. as depicted in FIG. 12) may be coupled to the elongated member via a second elongated member 430 (e.g., a cord, as depicted in FIG. 3A) and a coupling member 440 (e.g., as depicted in FIG. 11). The coupling member may be coupled (e.g., directly attached to the second elongated member and the second elongated member may be coupled (e.g., directly attached) to the gripping member. The coupling member 440 may be coupled to the elongated member 300 (e.g., via an opening 440a as depicted in FIG. 11) such that the coupling member is freely positionable along the elongated member. A second opening 440b (e.g., as depicted in FIG. 11) in the coupling member may be used to couple the second elongated member 430.

In some embodiments, the orthotic device may include at least one support member 450 (e.g., as depicted in FIGS. 1A-B and 2A-B) with each end of the at least one support member coupled to or couplable to the elongated band. The support member(s) may function to inhibit movement, during use, of the elongated band outside of the chest area. During use the support members may drape over one or more shoulders of the subject such that the elongated band is suspended, even in an inactivated state, is suspended/positioned around a subject's chest area.

In some embodiments, the at least one support member comprises an adjustable length relative to the elongated band such that differently sized subjects may be accommodated. In some embodiments, the orthotic device may include two support members with each support member draped over a different shoulder of a subject. In some embodiments, a first end of a support member may be couplable to the elongated band adjacent a midpoint area of the elongated band. The second end of the support member may be couplable adjacent an end of the elongated band or a base.

A method of using an orthotic device described herein may include limiting expansion of a subject's chest. The method may include positioning an elongated band substantially around a chest of a subject such that a first end of the elongated band is positioned adjacent a second end of the elongated band. The method may include applying a force to an elongated member of a pulley assembly away from a first and a second routing member. The method may include decreasing a distance between the first and the second routing members as a result of the applied force. The method may include inhibiting movement of the elongated member relative to at least one of the routing members such that the distance is inhibited from increasing by activating a locking mechanism.

In some embodiments, the orthotic device described herein may be fixed in any position and create any desired tension/counter pressure. This goal may be achieved by designing a pulley assembly which contains a locking element as described herein. The switch in combination with a curtain chain rope may make the sternum-band fixable. The orthotic device may be fixed with the pulley system on maximum tension level (i.e., the band provides maximum counter pressure to the wound), or fixed in a position with the bands' tension less strong and then the orthotic device may still be operated by squeezing the two grips together (in some embodiments), giving more counter pressure only at the moments when needed or desired.

In some embodiments, the orthotic device described herein may be used by any gender. In the case of very large-breasted women, the moving parts should be small and flexible. In this case, the grips may be detached and used with an adaptable part, leaving the housing which forms into a shape similar to a 'bridge' out. The bridge shape (e.g., as depicted in FIGS. 3B-C) allows the position of the moving parts to be several centimeters above as well as to the left and right of the area of the wound and thus the moving parts are inhibited from contacting the painful wound area. The bridge may be designed in two equal parts and can be opened and closed in the middle (e.g., as depicted in FIG. 4B). In this way, the two parts can click together making a complete unit. This configuration may allow easy access to the wound for care by doctors and nurses and which is open at the area of the wound so that caretaker can see the wound even when patient is wearing the band. This goal was achieved by with a 'bridge' with two moving parts so the wound is not visibly covered during use.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An orthotic device configured to limit expansion of a subject's chest, comprising:
    an elongated band which wraps, during use, around a chest of a subject comprising a first end and a second end;
    a first base configured to be removably coupled to the first end of the elongated band;
    a second base configured to be removably coupled to the second end of the elongated band; and
    a pulley assembly comprising: a first routing member removably coupled to the first base;
    a second routing member removably coupled to the second base;
    an elongated member coupling the first routing member to the second routing member by routing the elongated member through a plurality of first and second openings in the respective first and second routing members such that by applying, during use, a force to the elongated member away from the routing members, a distance between the first and the second routing members decreases, the elongated member extending between the first and second routing members in a first direction;

a locking mechanism which when activated inhibits, during use, movement of the elongated member relative to at least one of the routing members such that the distance is inhibited from increasing, wherein the locking mechanism comprises a movable portion, formed as part of the first routing member or the second routing member, which activates the locking mechanism during use by engaging a larger diameter portion of the elongated member in an interference fit with the moveable portion; and a handle adapted for drawing the elongated member in a second direction perpendicular to the first direction for decreasing the distance between the first and second routing members.

2. The orthotic device of claim 1, wherein the locking mechanism is coupled to the first routing member.

3. The orthotic device of claim 1, wherein the locking mechanism moves, during use, between a locked position to an unlocked position.

4. The orthotic device of claim 1, wherein decreasing the distance between the routing members moves the elongated band from an expanded state to a contracted state, and wherein when the elongated band is in the contracted state the first and the second end of the elongated band are drawn towards each other limit expansion of a subject's chest.

5. The orthotic device of claim 1, wherein the elongated band comprises a single continuous band of flexible material.

6. The orthotic device of claim 1, wherein the elongated band comprises a single continuous band of inelastic material.

7. The orthotic device of claim 1, wherein the first base comprises a first grip and a first grip base and the second base comprises a second grip and a second grip base.

8. The orthotic device of claim 7, wherein the first grip is positionable relative to the first grip base, and wherein the first grip is configured to be removably coupled to the first end of the elongated band.

9. The orthotic device of claim 1, wherein the first routing member is couplable to the first base by positioning a portion of the routing member within a complementary shaped opening in the first base.

10. The orthotic device of claim 1, wherein the elongated member comprises a pattern of alternating first and second diameters, wherein the second diameter is less than the first diameter.

11. The orthotic device of claim 10, wherein the locking mechanism comprises an opening with a third diameter and a fourth diameter, wherein the third diameter is greater than the first diameter, and wherein the fourth diameter is less than the first diameter and greater than the second diameter.

12. The orthotic device of claim 10, wherein the larger first diameter portions of the elongated member comprises substantially spherical beads coupled to and/or formed with the elongated members.

13. The orthotic device of claim 1, further comprising a handle coupled to the elongated member positioned between the first and the second routing member.

14. The orthotic device of claim 1, further comprising at least one support member with each end of the at least one support member coupled to or couplable to the elongated band.

15. The orthotic device of claim 1, further comprising at least one support member with each end of the at least one support member coupled to or couplable to the elongated band such that the at least one support member inhibits movement, during use, of the elongated band outside of the chest area.

16. The orthotic device of claim 1, further comprising at least one support member with each end of the at least one support member coupled to or couplable to the elongated band such that the at least one support member inhibits movement, during use, of the elongated band outside of the chest area, wherein the at least one support member comprises an adjustable length relative to the elongated band such that differently sized subjects may be accommodated.

17. The device of claim 1 wherein the locking mechanism engages the smaller diameter opening in an interference with the larger diameter portion of the elongated member by disposing the smaller diameter opening perpendicular to the elongated member.

18. The device of claim 1 wherein the locking mechanism engages a smaller diameter opening with the larger diameter portion of the elongated member by slideably engaging the moveable portion by disposing the moveable portion in a direction perpendicular to the movement of the elongated member.

19. The device of claim 1 wherein the locking mechanism engages a smaller diameter opening with the larger diameter portion of the elongated member by slideably engaging the moveable portion by rotationally pivoting the moveable portion perpendicular to a direction of travel of the elongated member.

20. The device of claim 1, wherein an applied force to the routing member in the perpendicular direction for temporarily decreasing the distance between the first and second routing members allows the decreased distance to return following the applied force.

21. A method of limiting expansion of a subject's chest, comprising:

positioning an elongated band around at least a portion of a chest of a subject such that a first end of the elongated band is positioned adjacent a second end of the elongated band, wherein the first end of the elongated band is removably coupled to a first base, wherein the second end of the elongated band is removably coupled to a second base;

applying a force to an elongated member of a pulley assembly away from a first routing member and a second routing member, wherein the first routing member is removably coupled to the first base, wherein the second routing member is removably coupled to the second base, and wherein the elongated member couples the first routing member to the second routing member by routing the elongated member through at least one of a plurality of first and second openings in the respective first and second routing members, the elongated member extending between the first and second routing members in a first direction;

decreasing a distance between the first and the second routing members as a result of the applied force to a handle adapted for drawing the elongated member in a second direction perpendicular to the first direction for decreasing the distance between the first and second routing members;

moving a movable portion of a locking mechanism such that the elongated member is moved from a first opening with a first diameter to a second opening with a second smaller diameter, wherein the first and second openings are formed in the movable portion and the movable portion is formed as part of the first routing member or the second routing member; and inhibiting movement of the elongated member relative to at least one of the routing members by engaging a larger diameter portion of the elongated member in an interference fit with the second opening such that the distance is inhibited from increasing by activating a locking mechanism.

22. The method of claim 21, wherein the elongated member comprises a pattern of alternating third and fourth diameters, wherein the fourth diameter is less than the third diameter, wherein the first diameter is greater than the third diameter, and wherein the second diameter is less than the third diameter and greater than the fourth diameter.

23. The method of claim 21, further comprising positioning the elongated band around at least a portion of the chest of the subject such that a first end of the elongated band is positioned adjacent a second end of the elongated band adjacent a front of a subject's chest.

24. An orthotic device configured to limit expansion of a subject's chest, comprising:

an elongated band which wraps, during use, around a chest of a subject comprising a first end couplable to a first base and a second end couplable to a second base;

a pulley assembly comprising: a first routing member removably coupled to the first base; a second routing member removably coupled to the second base; an elongated member coupling the first routing member to the second routing member, the elongated member extending between the first and second routing members in a first direction, such that by applying, during use, a pulling force to the elongated member a distance between the first and the second routing members decreases in response to a handle adapted for drawing the elongated member in a second direction perpendicular to the first direction for decreasing the distance between the first and second routing members;

a locking mechanism which when activated inhibits, during use, movement of the elongated member relative to at least one of the routing members such that the distance is inhibited from increasing, wherein when a movable portion of the locking mechanism is activated the elongated member is moved from a first opening with a first diameter to a second opening with a second smaller diameter, and wherein the first and second openings are formed in the moveable portion and the moveable portion is formed as part of the first routing member or the second routing member, which activates the locking mechanism during use by engaging a larger diameter portion of the elongated member in an interference fit with the moveable portion.

25. The orthotic device of claim 24, wherein the locking mechanism comprises a securing mechanism which inhibits inactivation of the locking mechanism once activated.

* * * * *